United States Patent
Kexin

[19]

[11] Patent Number: 6,026,313
[45] Date of Patent: Feb. 15, 2000

[54] METHOD OF AND APPARATUS FOR MEASURING VITAL TISSUE

[75] Inventor: Xu Kexin, Kyoto, Japan

[73] Assignees: Kyoto Dai-Ichi Kagaku Co., Ltd., Kyoto; Kabushiki Boseki Kabushiki Kaisha, Okayama, both of Japan

[21] Appl. No.: 09/132,259

[22] Filed: Aug. 11, 1998

[30] Foreign Application Priority Data

Aug. 20, 1997 [JP] Japan ................................. 9-240497
Mar. 4, 1998 [JP] Japan ................................. 10-071488

[51] Int. Cl.[7] ........................................................ A61B 5/00
[52] U.S. Cl. ............................................. 600/310; 600/309
[58] Field of Search ..................................... 600/309, 310, 600/322, 323, 335, 340, 344, 473, 476

[56] References Cited

U.S. PATENT DOCUMENTS

| | | |
|---|---|---|
| 4,726,382 | 2/1988 | Boehmer et al. . |
| 5,449,627 | 3/1996 | Steuer . |
| 5,830,132 | 11/1998 | Robinson ........................... 600/310 |

FOREIGN PATENT DOCUMENTS

| | | |
|---|---|---|
| 0 638 281 | 2/1995 | European Pat. Off. . |
| 0 706 776 | 4/1996 | European Pat. Off. . |

*Primary Examiner*—Eric F. Winakur
*Attorney, Agent, or Firm*—Nikaido Marmelstein Murray & Oram, Ltd.

[57] ABSTRACT

A fixture is provided on a set probe and a hole of the set probe communicates with that of the fixture so that a measuring probe consisting of an optical fiber bundle is inserted in the holes. A measured object is irradiated with light from a forward end of the measuring probe, so that outgoing light from the measured object enters the measuring probe. An air pack for coming into contact with the measured object is provided on the forward end of the measuring probe in a position not hindering emission and incidence of light. The air pack is connected with a pressure sensor, so that an indicator reads the pressure. Pressing force of the measuring probe is so adjusted that the pressure is at a constant value which is set for each measured object

18 Claims, 10 Drawing Sheets

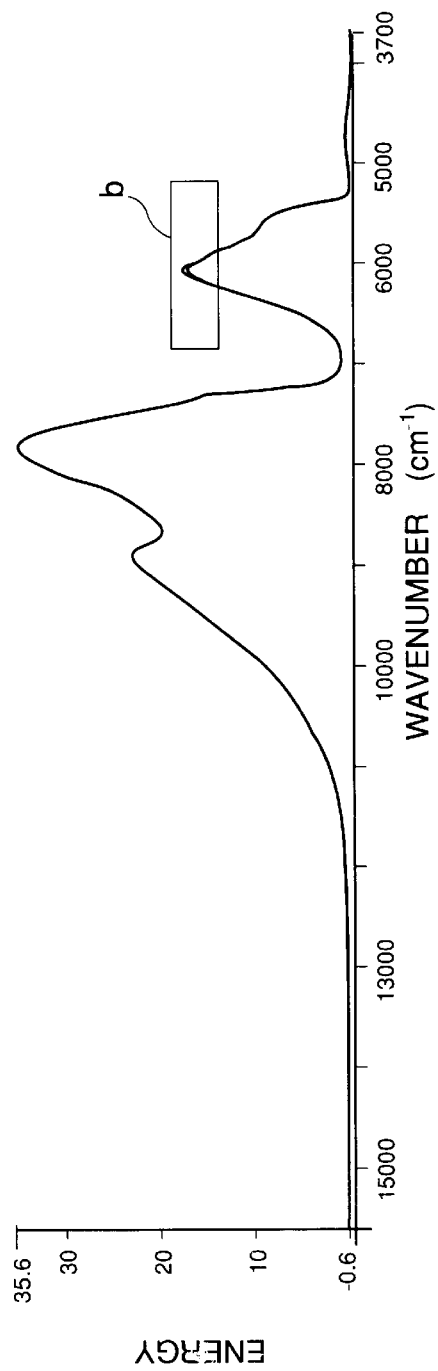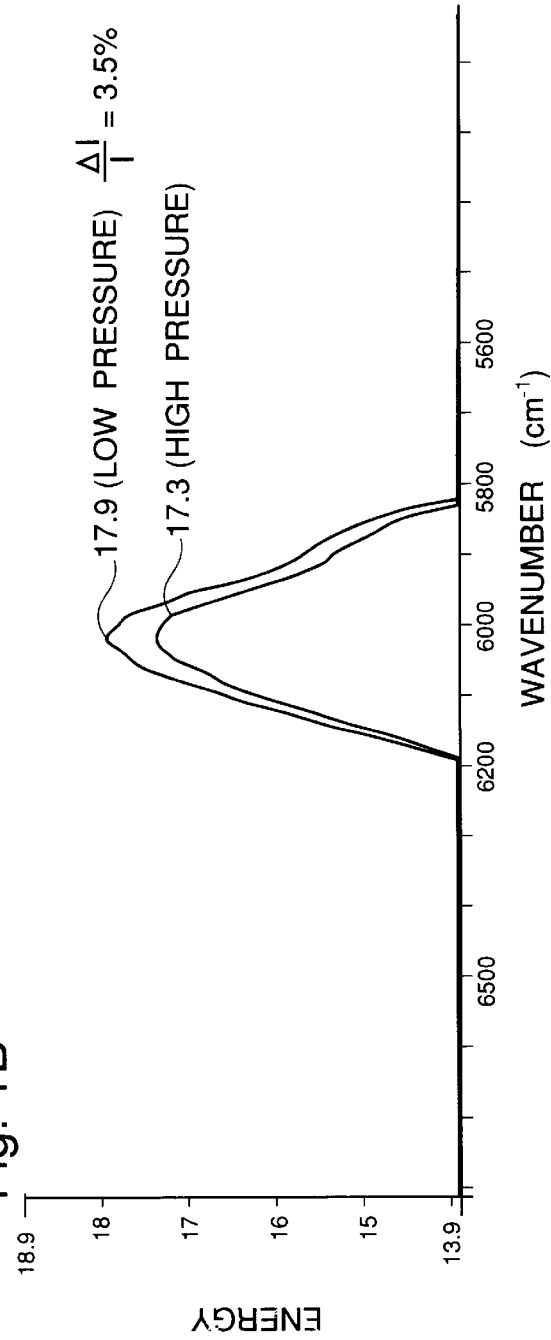
Fig. 1A
Fig. 1B

GRAVITATIONAL DIRECTION ↓

MEASURING DIRECTION →

METHOD OF AND APPARATUS FOR MEASURING VITAL TISSUE

BACKGROUND OF THE INVENTION

1. Field of the Invention

The present invention relates to a method of measuring a physical quantity of a vital tissue by bringing a probe for measuring the physical quantity into contact with the vital tissue and a measuring apparatus therefor. Specifically, it relates to a non-invasive measuring method: irradiating a human body with light of a near infrared region and measuring a physical quantity in the human body such as the hematic glucose concentration or the hemal oxygen saturation using output light from the human body resulting from the light, and a measuring apparatus employed therefor. The output light from the human body includes all light such as transmitted light, scattered light or reflected light outputted from the human body after the same is irradiated with light.

2. Description of the Prior Art

A non-invasive measuring method of irradiating an organism with light and measuring hemal oxygen saturation or a blood-sugar level from resultant output light has been undertaken in the field of clinical tests. The organism is a scatterer having an internal structure complicatedly varying with portions, and hence the optical path length of the light in the organism must be kept constant in order to measure concentration such as the blood-sugar level. In the case of bringing a measuring probe into contact with a vital tissue and irradiating the same with light for measuring resultant output light, no reproducible measured value can be obtained unless conditions such as the position of the vital tissue to be in contact with the measuring probe and the orientation of the measuring probe are settled.

A non-invasive measuring apparatus, for measurements by pressing an optical measuring device against a vital tissue with a mounting apparatus, has been proposed (refer to Japanese Patent Laying-Open Gazette No. 8-215180 (1996) (cited reference)). In this measuring apparatus, a sensor is pressed to come in contact with the vital tissue vertically downward from above the vital tissue.

In the case of pressing a measuring probe against an arm or a finger of a human body for measurements, the measured portion readily varies with the posture of the human in the gravitational direction (i.e., the vertical direction). Such vertical variation of the measured portion may change the pressure of the measuring probe pressed against the measured portion, depending on the position for bringing the measuring probe into contact with the arm or finger. It is known that the intensity of scattered light from a vital tissue changes if the pressure of a measuring probe coming into contact with the vital tissue changes to cause an error in the measured value particularly in the case of measuring the blood volume or a physical quantity related to blood.

There are data obtained as to how much measured values of an organism vary with the pressure. FIGS. 1A and 1B show data obtained by pressing an optical fiber probe against a single position of a finger, irradiating the finger with light from the optical fiber probe and changing the pressure (contact pressure) of the optical fiber probe pressed against the finger for measuring the intensity of resultant reflected light FIG. 1A shows a spectrum over a wide wavenumber range, and FIG. 1B is an enlarged view of a portion (b) in FIG. 1A around 6000 cm$^{-1}$.

In the data shown in FIGS. 1A and 1B, the reflected light relatively changes by 3.5% between low and high pressures. Conversely, FIG. 2 shows a result of transmission absorption measurement of a glucose solution performed for inferring how much a light quantity changes in the case of optically measuring a blood-sugar level. For example, relative change of the light intensity corresponding to a concentration change of 10000 mg/dl is about 2.5% at a glucose absorption wavelength of 1679 nm (about 6000 cm$^{-1}$). Since the variation range of glucose concentration within the physiological variation range of a human body is 400 mg/dl, it comes to that there is only relative change of light quantity of 0.1% in terms of the relative change of light absorption intensity by glucose. Namely, it comes to that this relative change of the reflected light resulting from the contact pressure is 35 times the variation range of glucose concentration.

Even if an arm or the like is so fixed that the measuring probe is pressed against a constant portion, it comes to that the measured value also changes if the contact pressure between the measured probe and the vital tissue varies with change of the vertical posture and no reproducible measurement result can be obtained.

In the apparatus described in the cited reference pressing the measuring probe vertically against the organism, change of the posture of the organism or the like appears as that of the contact pressure between the measuring probe and the vital tissue, and it is difficult to obtain a result having excellent reproducibility.

SUMMARY OF THE INVENTION

The object of the present invention is to obtain a reproducible measurement result by fixing a measured position of an organism and settling the contact pressure of a measuring probe which is pressed against the measured portion.

The measuring method according to the present invention is adapted, when bringing a measuring probe for physical quantity measurement into contact with a vital tissue for the measuring of a physical quantity of the vital tissue, to suppress pressure change in a direction (hereinafter referred to as a measuring direction) for pressing the measuring probe against the vital tissue, resulting from change of the gravitational direction, by rendering the measuring direction and the gravitational direction not to come on the same straight line.

To this end, the inventive method comprises a step of fixing the periphery of a measured portion of the vital tissue thereby spatially fixing the measured portion, for measuring the physical quantity by bringing the measuring probe into contact with the measured portion under a constant pressure from a direction hardly influenced by gravity, preferably from the horizontal direction.

A model from which the present invention has been derived is now described with reference to FIGS. 3A and 3B.

As shown in FIG. 3A, a measuring probe 4 is pressed against a measured portion 2 such as a human finger. It is assumed that the measuring probe 4 so acts that the pressure against the measured portion 2 becomes zero at the origin. It is also assumed that the measured portion 2 has a circular section having a radius of curvature R around a center of curvature C. Assuming that "Xp" represents x-coordinates of a position (P) where the measuring probe 4 is in contact with the measured portion 2, "Yp" represents y-coordinates thereof, "Xc" represents x-coordinates of the center (C) of curvature of the measured portion 2, "Yc" represents y-coordinates thereof, "R" represents the radius of curvature, and "θ" represents an angle formed by a straight line connecting the center (C) of curvature and the position (P) where the measuring probe 4 is in contact with the measured portion 2 with respect to a horizontal plane, the following equations hold:

$$Xp = Xc + R \cdot \cos\theta$$
$$Yp = Yc + R \cdot \sin\theta \quad (1)$$

Assuming that "rp" represents the distance between the position (P) and the origin, the following equation holds:

$$rp^2 = Xp^2 + Yp^2$$
$$= Xc^2 + Yc^2 + 2R(Xc \cdot \cos\theta + Yc \cdot \sin\theta) + R^2 \quad (2)$$

It is assumed that only gravitational displacement dy results from the posture of a human. Differentiating equation (2), the following equation (3) is derived:

$$2rp \cdot drp = 2Yc \cdot dYc + 2R \cdot dYc \cdot \sin\theta \quad (3)$$

where "drp" represents the displacement of the measuring probe 4.

Assuming that change "dp" of the pressure of the measuring probe 4 acting on the measured portion 2 is proportional to the displacement "drp" of the measuring probe 4, "drp"=0 when measured under conditions of "θ"=0 and "Yc"=0 as understood from the equation (3), and influence exerted on the contact pressure by gravitational fluctuation "dYc" is minimized. Namely, it is understood that the most reproducible data can be obtained in such a state that the measured portion 2 is on the same y-coordinates as the origin and the measuring probe 4 is pressed against the measured portion 2 so that the angle "θ" is zero (horizontal direction).

The measuring apparatus according to the present invention for implementing such measuring conditions comprises a set probe having a shape corresponding to that of a peripheral portion of a measured portion of a vital tissue for fixing the peripheral portion excluding the measured portion, a measuring probe which is movably set on the set probe and fixed to the set probe in a state coming into contact with the measured portion of the vital tissue fixed to the set probe from a direction hardly influenced by gravity, preferably from a horizontal direction, and a fixture for fixing the measuring probe to the set probe.

In order to press the measuring probe against the measured portion with a constant pressure, the fixture preferably comprises means for setting a relative position of the measuring probe with respect to the set probe.

Furthermore, it is preferable that the measuring probe comprises a constant pressure generating mechanism on it's forward end portion coming into contact with the measured portion as means for pressing the measuring probe against the measured portion with a constant pressure, and further comprises a pressure sensor connected with the constant pressure generating mechanism. An air pack can be mentioned as an example of the constant pressure generating mechanism.

An example of the measuring probe is an optical measurement probe for irradiating the vital tissue with light, receiving output light from the vital tissue resulting from the light and non-invasively measuring a hematic component of the vital tissue.

In order to correctly position the measured portion, the set probe is preferably prepared in response to the shape of each measured object of the vital tissue.

In the case that the set probe is adapted to fix a finger of a human hand, the measuring apparatus preferably further comprises a support for obliquely supporting the lower arm between the elbow and the wrist while directing the elbow and the wrist downward and upward respectively, in order to suppress gravitational displacement of the measured portion.

Thus, the measuring apparatus according to the present invention is adapted to fix the periphery of the measured portion of the vital tissue for spatially fixing the measured portion and bringing the measuring probe into contact with the measured portion from the direction hardly influenced by gravity with a constant pressure for measuring the physical quantity. Consequently, it is possible to suppress pressure change in the measuring direction resulting from gravitational change. Even if the posture of the human to be measured slightly changes, it is possible to suppress change of the pressure of the measuring probe against the measured portion in the gravitational direction. Thus, dispersion of measured data resulting from contact pressure change can be suppressed, to be capable of obtaining measured data having excellent reproducibility.

The foregoing along with other objects, features, aspects and advantages of the present invention will become more apparent from the following detailed description of the present invention when taken in conjunction with the accompanying drawings.

BRIEF DESCRIPTION OF THE DRAWINGS

FIG. 1A shows a spectrum obtained by varying the pressure of an optical fiber probe pressed against a finger and measuring the intensity of reflected light, and FIG. 1B is an enlarged view showing a portion (b) in FIG. 1A around 6000 $cm^{-1}$;

DESCRIPTION OF THE PREFERRED EMBODIMENTS

Figure 2:
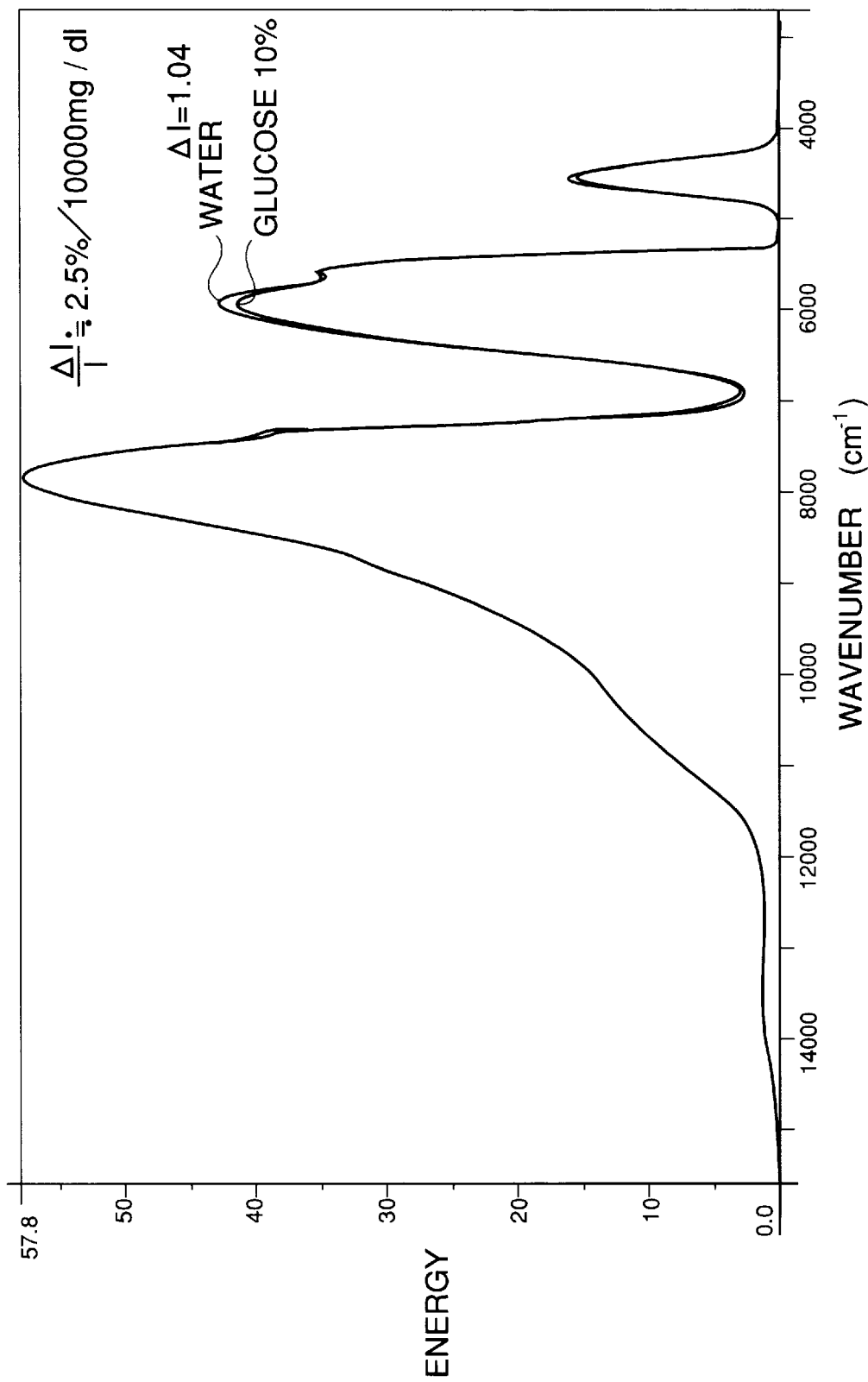
FIG. 2 illustrates a transmission absorption spectrum of a glucose solution.
Figure 3A:
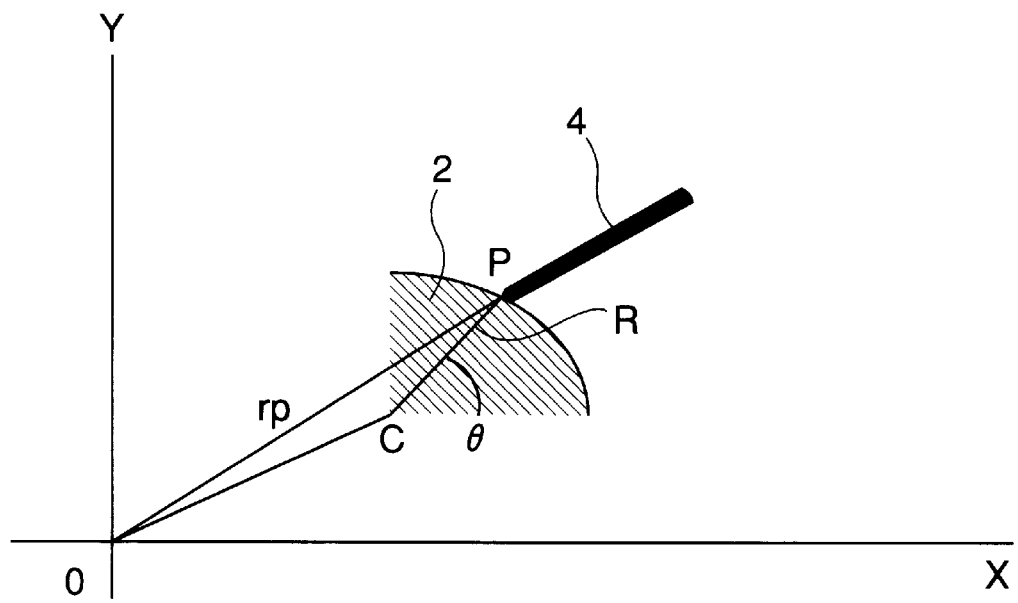
FIG. 3A illustrates a model for calculating the contact pressure between a measuring probe and a measured portion.
Figure 3B:
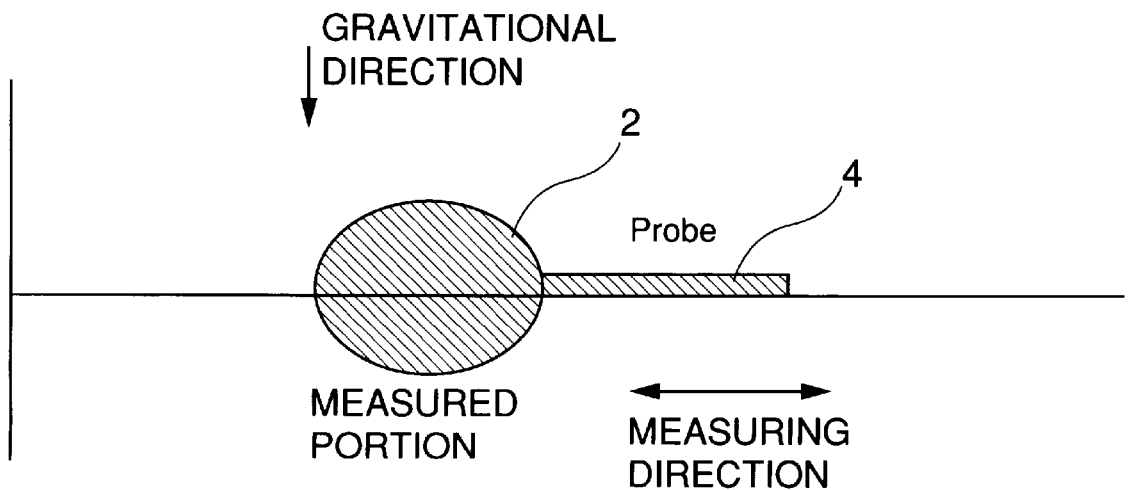
FIG. 3B is a front elevational view showing the relation between the measuring probe and the measured portion in such a state that contact pressure change is minimal.
Figure 4A:
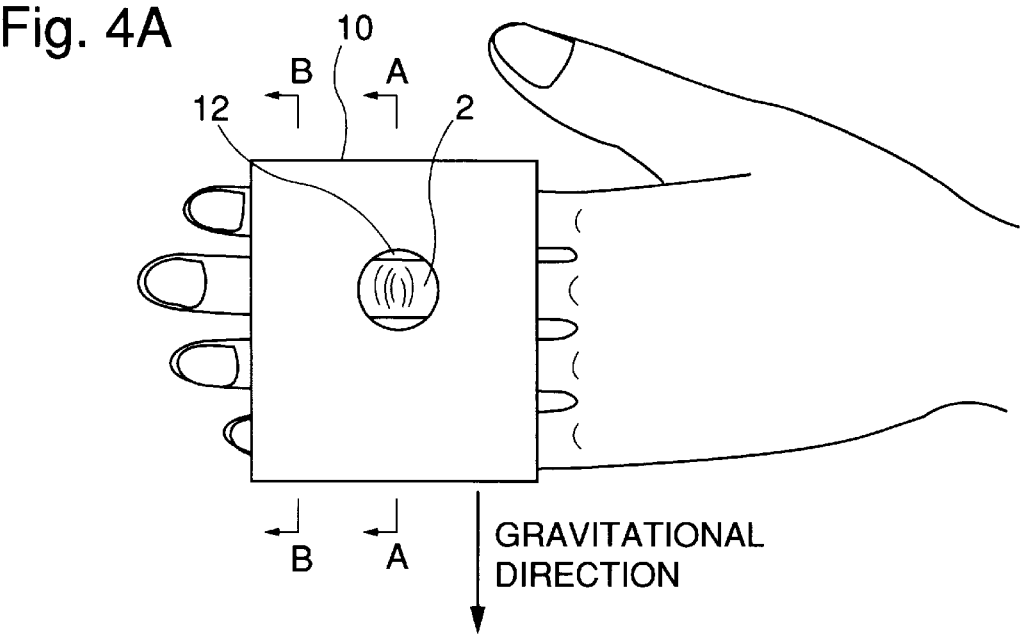
FIG. 4A is a front elevational view showing a hand, serving as a measured object, fixed to a set probe in a first embodiment of the present invention.
Figure 4C:
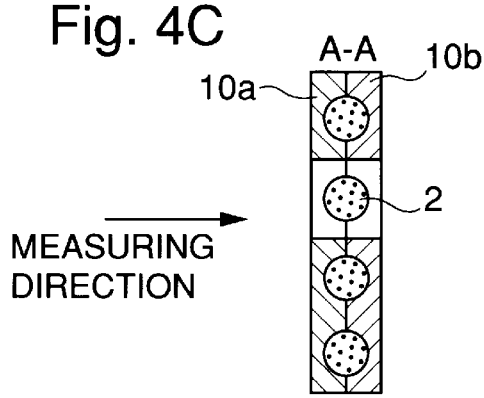
FIGS. 4C and 4D are sectional views taken along the lines A—A and B—B in FIG. 4A respectively.
Figure 4D:
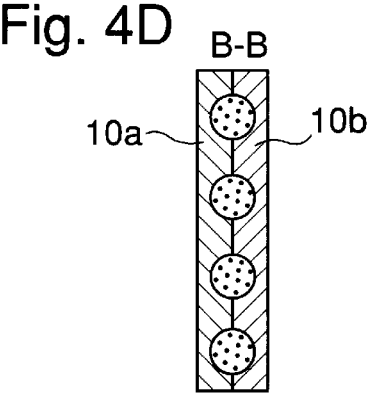
Figure 4B:
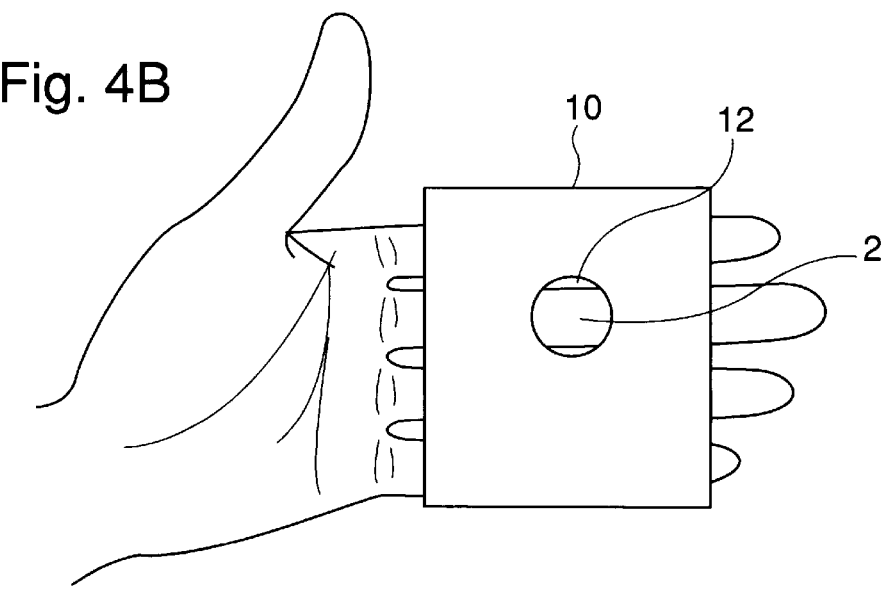
FIG. 4B is a rear elevational view thereof.

FIGS. 4A to 4D show the first embodiment of the present invention. FIGS. 4A and 4B are front and rear elevational views showing a human hand serving as a measured object 2 which is fixed to a set probe 10 respectively, and FIGS. 4C and 4D are sectional views taken along the lines A—A and B—B in FIG. 4A respectively. The human hand is adopted as the measured object 2 of a vital tissue.

The set probe 10, which is formed by combining two members 10a and 10b with each other, can hold and fix four fingers excluding the thumb. A hole 12 is formed in the set probe 10, for exposing a measured portion of a specific finger. The set probe 10 fixes the four fingers around the hole 12, thereby fixing the spatial position of the measured portion. It is assumed here that a part of the middle finger is employed as the measured portion, and the set probe 10 fixes the spatial position of the overall hand, not to be in contact with the measured portion itself.

Figure 5:
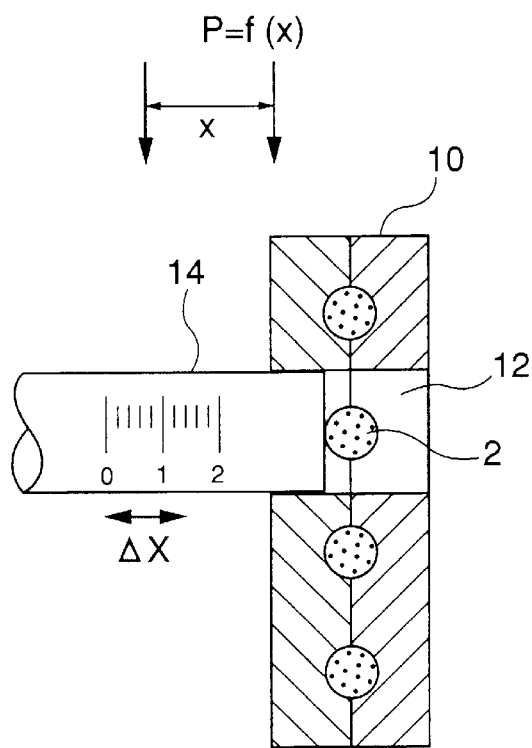
FIG. 5 is a sectional view showing the set probe and a measuring probe in the embodiment of the present invention.

Referring to FIGS. 4A and 4B, the set probe 10 fixes the fingers excluding the thumb to be horizontally directed and to vertically line up with each other. The set probe 10 is so formed that its spatial form is identical to the contour of the measured object 2. Therefore, different set probes 10 are prepared for different measured objects 2. A measuring probe (not shown) is horizontally inserted into the hole 12 of the set probe 10, to be in contact with the finger in the hole 12 for making measurement FIG. 5 shows an exemplary measuring probe 14. The measuring probe 14 consisting of an optical fiber bundle is formed with an outer diameter substantially equal to the inner diameter of the hole 12, and a scale is provided on the outer peripheral surface of the measuring probe 14 to be capable of setting a relative position from the set probe 10. In this embodiment, the contact pressure "P" between the finger of the measured object 2 and the measuring probe 14 is expressed as follows:

$$P=f(x)$$

as a function of a relative distance (x). When the relative distance (x) is set for each measured object 2 for measurements with this relative distance (x), the contact pressure P between the measuring probe 14 and the measured object 2 can be kept constant for obtaining a reproducible measured value.

Figure 6:
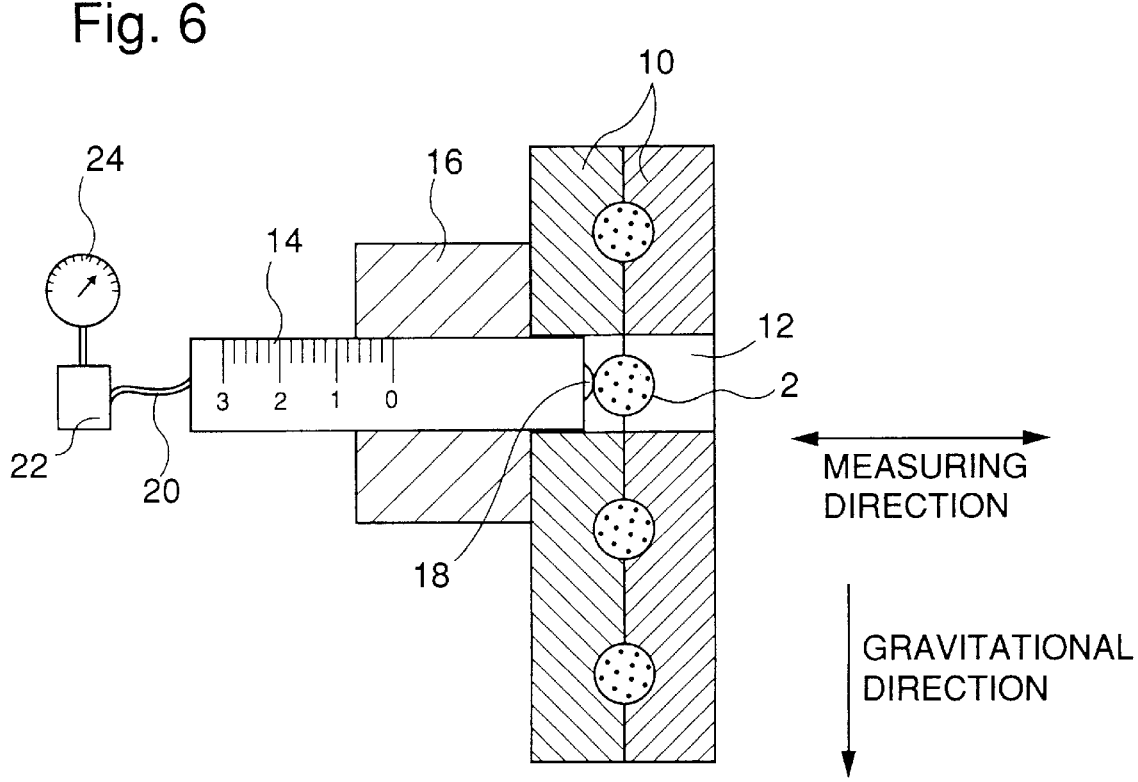
FIG. 6 is a sectional view showing a set probe and a measuring probe in another embodiment of the present invention.

FIG. 6 shows an embodiment of another means for keeping the contact pressure between a measuring probe 14 and a measured object 2 constant. A fixture 16 is provided on a set probe 10, and a hole 12 in the set probe 10 communicates with a hole in the fixture 16 so that the measuring probe (fiber probe) 14 consisting of an optical fiber bundle is inserted into the holes. The measured object 2 is irradiated with light from the forward end of the measuring probe 14, so that outgoing light from the measured object 2 enters the measuring probe 14. An air pack 18 for coming into contact with the measured object 2 is provided on the forward end of the measuring probe 14 in a position not hindering emission and incidence of the light. The air pack 18 is connected with a pressure sensor 22 through a tube 20 of polytetrafluoroethylene, for an indicator 24 to read the pressure.

In the embodiment shown in FIG. 6, fingers are fixed to the set probe 10 so that the measuring probe 14 is inserted into the hole of the fixture 16 for bringing the air pack 10 provided on its forward end into contact with the measured object 2, and the pressure sensor 22 directly detects the contact pressure. It is possible to regularly make measurements under a constant contact pressure by adjusting the pressing force of the measuring probe 14 so that the pressure is at a constant level which is set for the measured object 2.

Figure 7A:
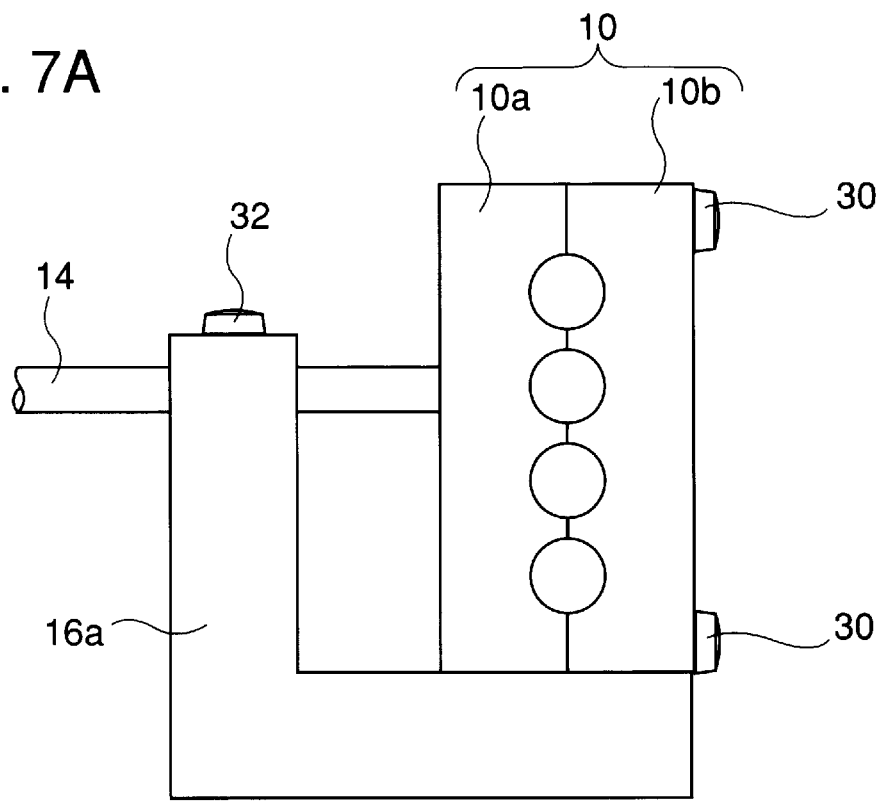
FIG. 7A is a front elevational view showing an exemplary fixture for the fixing of the measuring probe to the set probe.
Figure 7B:
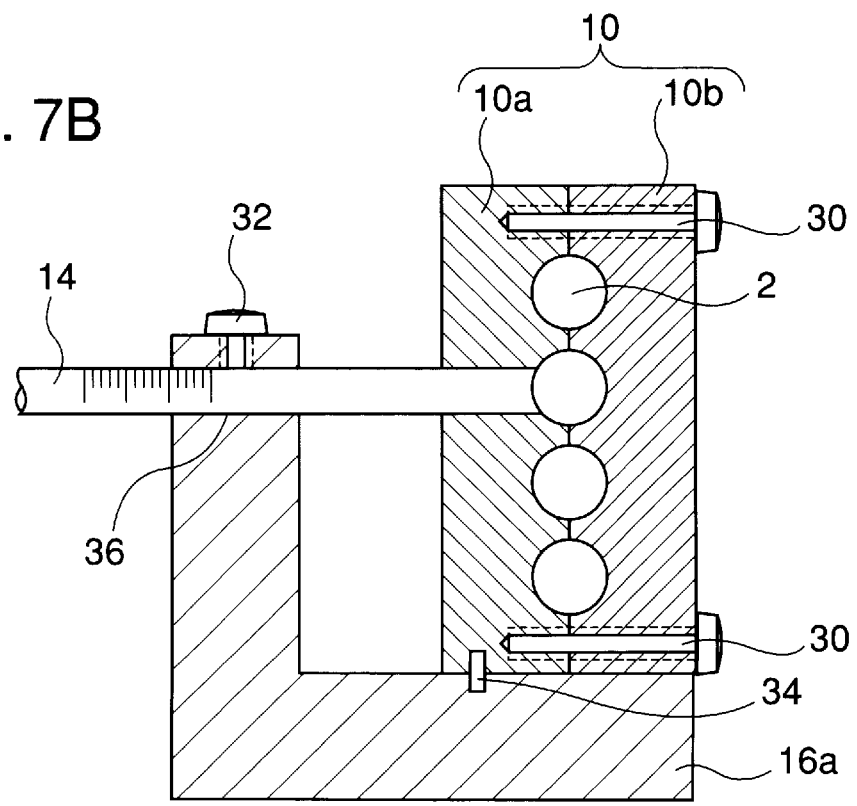
FIG. 7B is a sectional view thereof.

FIGS. 7A and 7B are a front elevational view and a sectional view showing an exemplary fixture 16a for fixing the measuring probe 14 to the set probe 10.

Two pin holes are formed on a lower portion of the member 10a forming the set probe 10. A pin 34 provided on a substrate surface of the L-shaped fixture 16a is fitted in either pin hole, thereby relatively positioning the member 10a of the set probe 10 on the fixture 16a. Positioning accuracy for the member 10a and the fixture 16a is guaranteed by working accuracy for the member 10a, the fixture 16a, and the pin 34. The other member 10b forming the set probe 10 is relatively positioned with respect to the member 10a by a pin (not shown) and fixed by screws 30, whereby the set probe 10 is assembled and fixed to a prescribed position of the fixture 16a. The set probe 10, which is merely fixed to the fixture 16a by the pin 34, can be readily detached.

An upright portion of the L-shaped fixture 16a is provided with a hole 36 to receive the measuring probe 14 in order to fix the measuring probe 14 while keeping a prescribed association between the same and the set probe 10, and a screw hole is provided to communicate with this hole 36 from above. A screw 32 inserted in the screw hole fixes the measuring probe 14 to the fixture 16a. The measuring probe 14 is inserted in the hole 36 of the fixture 16a, so that the relative positional association between the measured probe 14 and the set probe 10 is adjusted through a scale provided on the measuring probe 14 and fixed by the screw 32. A pressure sensor previously measures the association between the scale and the pressure.

Figure 8A:
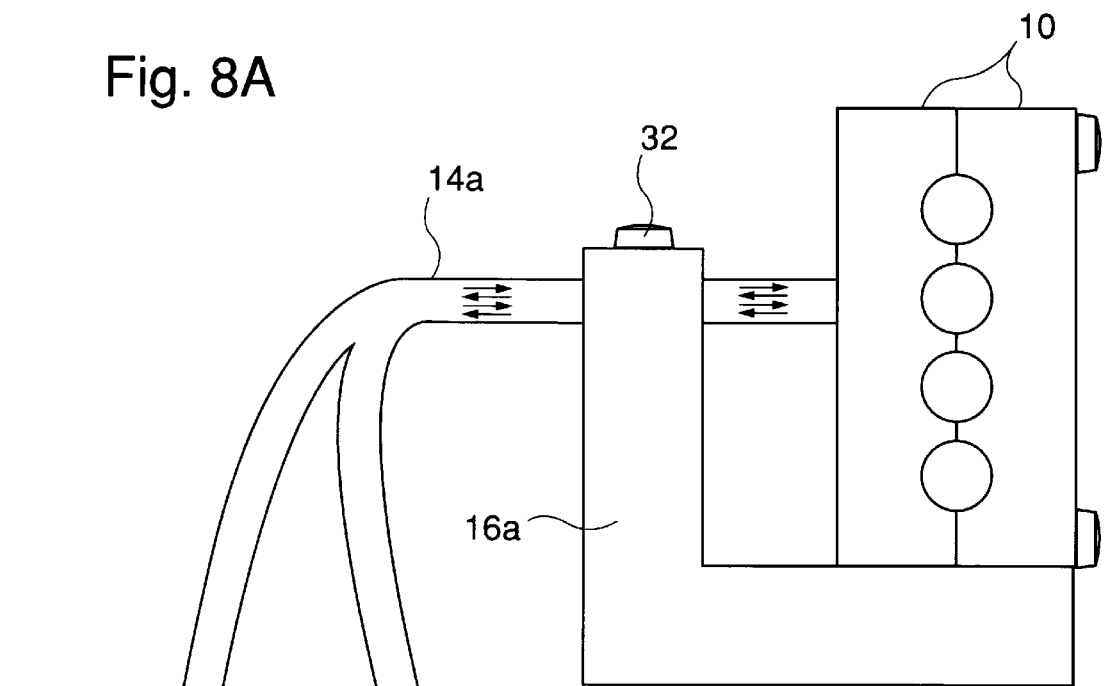
FIG. 8A is a block diagram schematically showing a system for the measuring of the physical quantity in a measured object.

FIG. 8A schematically shows a system for measuring the physical quantity of a measured object A measuring probe 14a is prepared from a biforked optical fiber bundle. A single end of the measuring probe 14a comes into contact with the measured object, while biforked end portions thereof serve as a light source side and a photoreceiving part side respectively. Light emitted from a light source part 40 enters the light source side end portion of the measuring probe 14a through a spectroscopic part 42 as monochromatic light. The photoreceiving part side end portion of the measuring probe 14a is connected to a photoreceiving part 44, and light detected by the photoreceiving part 44 is converted to an electric signal and amplified by a data processing part 46. A control calculation part 48 controls the respective parts and operates a digital signal from the data processing part 46 for the calculating of a noted physical quantity such as hematic component concentration. An output part 50 is a display such as a CRT or a printer outputting the result of calculation of the physical quantity by the control calculation part 48.

In this measuring system, the light from the light source part 40 is converted to monochromatic light through the spectroscopic part 42 to enter the light source side end portion of the measuring probe 14a, to be applied to the measured object which is fixed to a set probe 10 from the single end of the measuring probe 14a. Output light from the measured object irradiated with the light enters the measuring probe 14a and further enters the photoreceiving part 44 from the photoreceiving side end portion, to be detected and amplified by the data processing part 46, so that the control·calculation part 48 obtains the physical quantity.

Figure 8B:
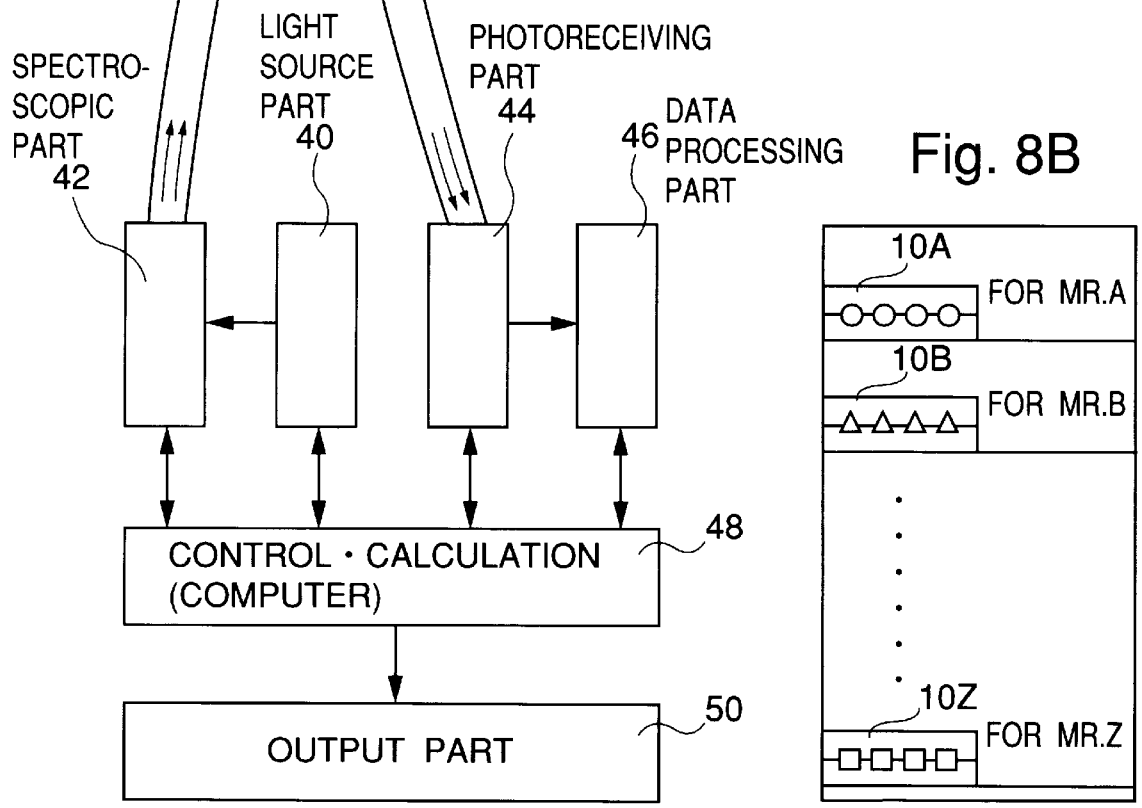
FIG. 8B is a schematic front elevational view showing such a state that different set probes are prepared.

FIG. 8B shows such a state that different set probes 10A to 10Z are prepared for different measured persons respectively. Each of the set probes, 10A to 10Z, which are fitted in either pin of the fixture 16a to be detachably fixable as shown in FIG. 7B, is readily exchangeable.

Figure 9:
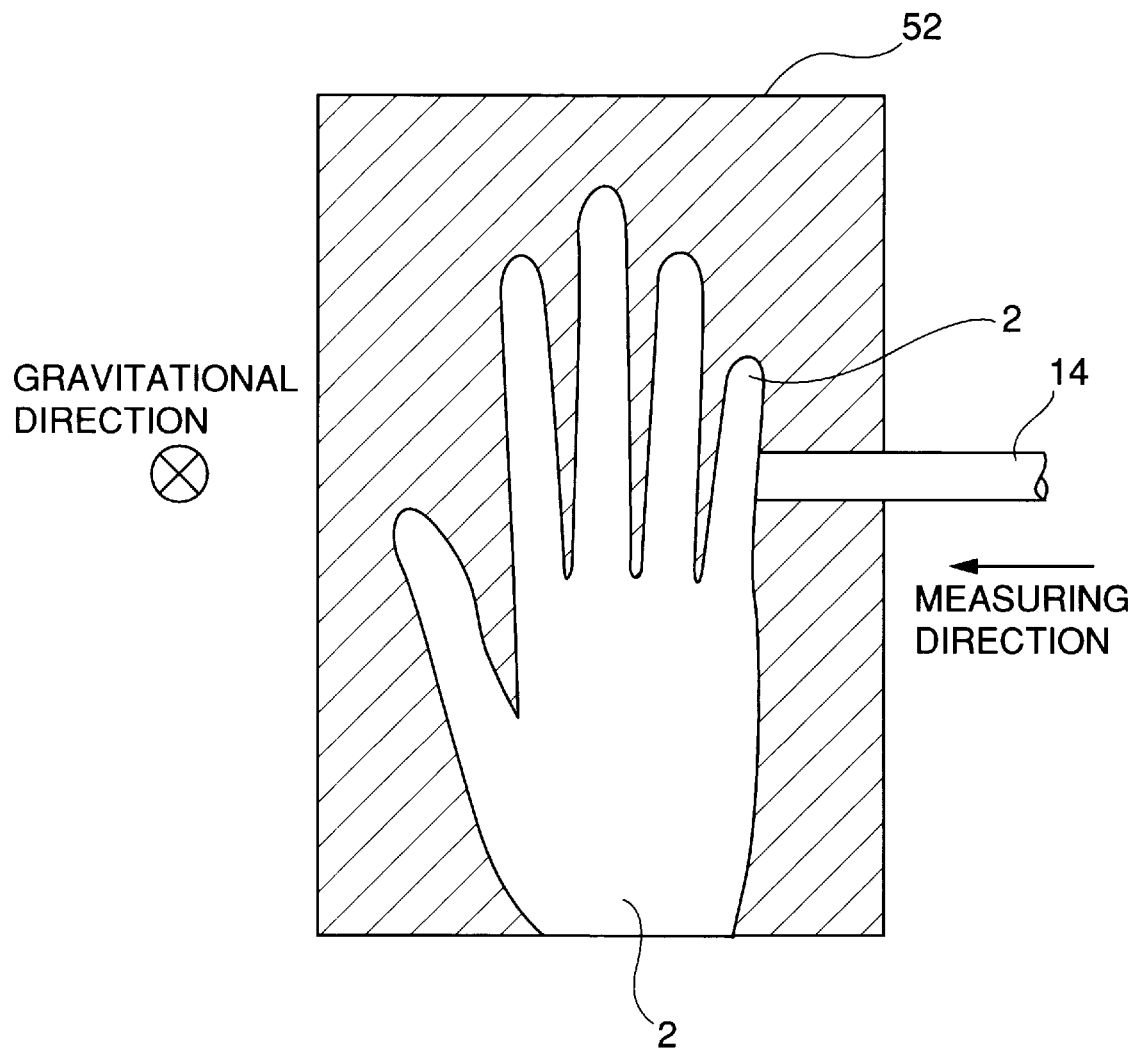
FIG. 9 is a sectional view showing a set probe and a measuring probe in still another embodiment of the present invention.

FIG. 9 shows an example arranging a finger serving as a measured object 2 on a horizontal plane. A set probe 52 is provided with a depression for fixing a hand being the measured object 2, and a hole communicating with the depression from the exterior. A measuring probe 14 is inserted in the hole to be pressed against and brought into contact with the finger of the hand from the horizontal direction.

Figure 10A:
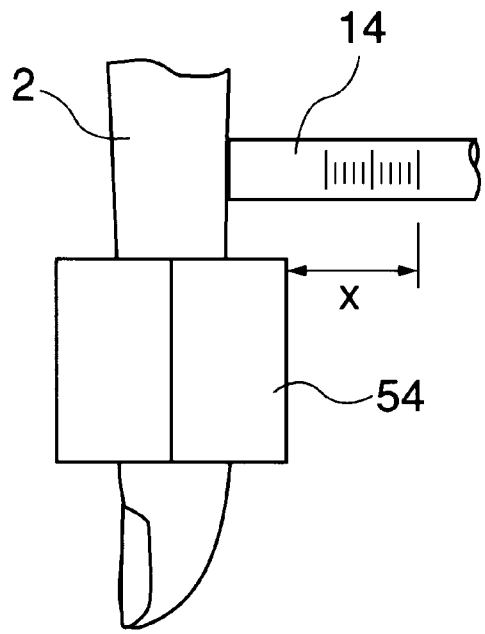
FIGS. 10A to 10C are sectional views showing set probes and measuring probes in further embodiments of the present invention respectively.
Figure 10B:
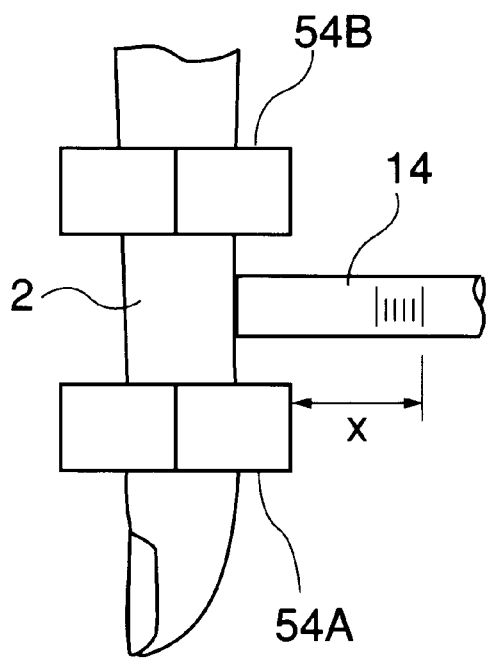
Figure 10C:
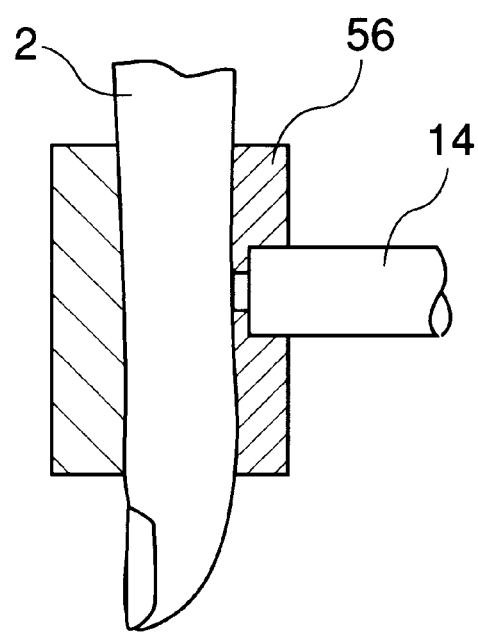

FIGS. 10A to 10C show some further embodiments of set probes and measuring probes for employing fingers as measured objects 2.

Referring to FIG. 10A, a set probe 54 is provided in the form of a ring to fit a single finger 2, so that the measuring probe 14 provided with a scale for setting a relative position with respect to the set probe 54 is capable of coming into contact with the finger 2.

Referring to FIG. 10B, a pair of set probes 54a and 54b are provided to be capable of fixing the finger 2 in two portions. The measuring probe 14, which comes into contact with the finger 2 between the set probes, 54a and 54b, is provided with a scale to be capable of setting a relative distance "x" between the measuring probe 14 and the set probe 54a.

Referring to FIG. 10C, the set probe 56 to fix a single finger 2 is provided with a hole so that a measuring probe 14 is inserted into the hole.

Figure 11:
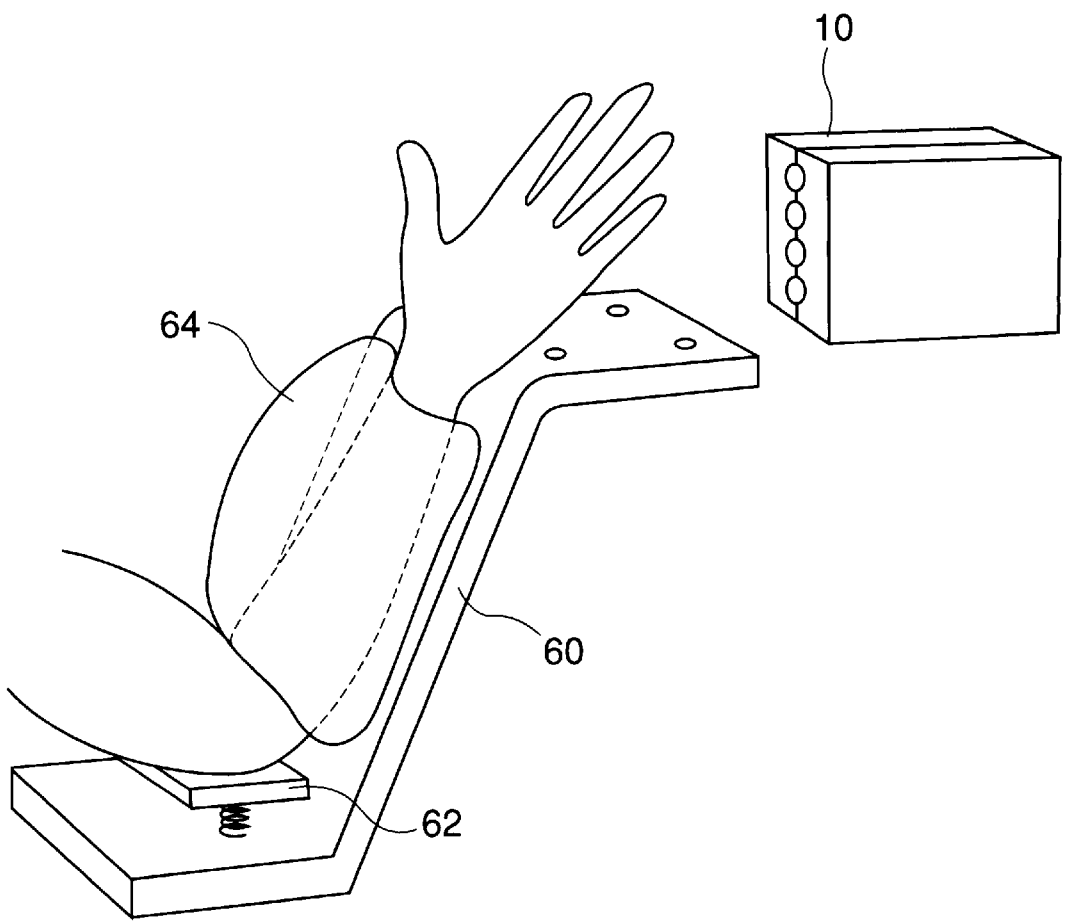
FIG. 11 is an exploded perspective view showing a set probe and a supporter in a further embodiment of the present invention.

FIG. 11 shows a further embodiment of the present invention. Referring to FIG. 11, the set probe 10 is similar to that shown in FIGS. 4A to 4D. A supporter 60 to hold the set probe 10 as well as an arm is inclined to be capable of obliquely supporting the lower arm while directing the elbow and the wrist downward and upward respectively. An adjuster 62 is provided on a lower portion of the supporter 60 located under the elbow, in order to adjust the vertical position of the elbow in response to the length of the lower arm.

A presser member 64 is mounted in order to fix the arm while supporting the same on the supporter 60. The presser member 64 is formed with a soft bag filled up with air, in order not to influence the blood flow of the arm.

When the supporter 60 shown in FIG. 11 is employed, it is possible to inhibit the arm from vertical displacement resulting from change of posture, thereby making measurements with excellent reproducibility.

Although the present invention has been described and illustrated in detail, it is clearly understood that the same is by way of illustration and example only and is not to be taken by way of limitation as the spirit and scope of the present invention is limited only by the terms of the appended claims.

I claim:

1. A method of measuring a vital substance in a vital tissue, the method comprising
    fixing a periphery of a portion of a vital tissue to be measured to spatially fix the portion to be measured;
    contacting a measuring probe with the portion to be measured under a constant pressure from only a horizontal direction; and
    measuring a vital substance in the vital tissue using the measuring probe.

2. A measuring apparatus suitable for measuring a vital substance in a vital tissue, the apparatus comprising
    a set probe which is configured to contact a periphery of a portion of a vital tissue to be measured while excluding contacting the portion to be measured, to spatially fix the portion to be measured;
    a measuring probe which is movably disposed in and reversibly fixable to the set probe, wherein the measuring probe is configured to contact with the portion to be measured from only a horizontal direction; and
    a fixture for reversibly fixing the measuring probe to the set probe.

3. The measuring apparatus of claim 2, wherein the measuring probe comprises means for setting a relative position of the measuring probe with respect to the set probe.

4. The measuring apparatus of claim 3, wherein the means comprises a scale which is provided on an outer peripheral surface of the measuring probe.

5. The measuring apparatus of claim 2, wherein the measuring probe comprises a constant pressure generating mechanism which is provided on a forward end portion of the measuring probe and is configured to contact with the portion to be measured, and a pressure sensor which is connected with the constant pressure generating mechanism.

6. The measuring apparatus of claim 5, wherein the constant pressure generating mechanism comprises an air pack.

7. The measuring apparatus of claim 2, wherein the measuring probe comprises an optical measurement probe suitable for irradiating the portion of the vital tissue to be measured with light, receiving output light from the portion of the vital tissue to be measured resulting from the irradiated light and non-invasively measuring a hematic component of the vital tissue.

8. The measuring apparatus of claim 7, wherein the measuring probe comprises a biforked optical fiber bundle, a spectroscopic part, a light source part, a photoreceiving part and a data processing part, wherein the measuring probe is configured such that light from the light source part passes through the spectroscopic part and enters a light source side end portion of the optical fiber bundle as monochromatic light to irradiate the portion to be measured, and output light received from the portion to be measured enters a photoreceiving part side end portion of the optical fiber bundle, passes into the photoreceiving part, is converted to an electric signal and is amplified in the data processing part.

9. The measuring apparatus of claim 2, wherein the set probe has been manufactured to have a shape which corresponds to the periphery of the portion of the vital tissue to be measured.

10. The measuring apparatus of claim 2, wherein the set probe comprises two reversibly connectable members which are configured to together fix four fingers of a human hand, wherein a hole is defined in the set probe to expose a portion to be measured of one of the four fingers, and the measuring probe is configured to be horizontally inserted into the hole to contact with the portion to be measured.

11. The measuring apparatus of claim 2, wherein the set probe is configured to fix fingers of a human hand, and the measuring apparatus further comprises a supporter which is configured to obliquely support a human arm between the elbow and the wrist while directing the elbow downward and the wrist upward, wherein the set probe is fixed to the supporter.

12. The measuring apparatus of claim 11, further comprising a presser member configured to fix the arm while exerting no influence on blood flow through the arm.

13. The measuring apparatus of claim 2, wherein a first hole is defined in the set probe, and a second hole is defined in the fixture and the measuring probe is configured to be inserted into the first and second holes.

14. The measuring apparatus of claim 2, wherein the fixture is an L-shaped structure which defines a first hole, wherein the measuring probe is configured to be inserted into the first hole, and a second hole which is a screw hole, and is located above and communicates with the first hole for fixing the measuring probe with a screw.

15. The measuring apparatus of claim 2, wherein the set probe is provided with a depression configured to fix a human hand and a hole is defined in the set probe which communicates with the depression and the hole exposes a finger to be measured, wherein the measuring probe is configured to be horizontally inserted into the hole to contact with the finger to be measured.

16. The measuring apparatus of claim 2, wherein the set probe is provided in the form of a ring which is configured to receive a forward end of a human finger, a scale is provided on a side surface of the measuring probe, and the measuring probe is fixed to the set probe in a position configured to contact with the forward end.

17. The measuring apparatus of claim 2, wherein the set probe is provided in the form of a pair of members which are configured to fix a human finger in two places, a scale is provided on a side surface of the measuring probe, and the measuring probe is fixed to the set probe in a position configured to contact with the finger between the pair of members.

18. The measuring apparatus of claim 2, wherein the set probe is configured to fix a human finger, a hole is defined in the set probe, and the measuring probe is configured to be inserted into the hole and contact with the finger.

* * * * *